Figure 1:
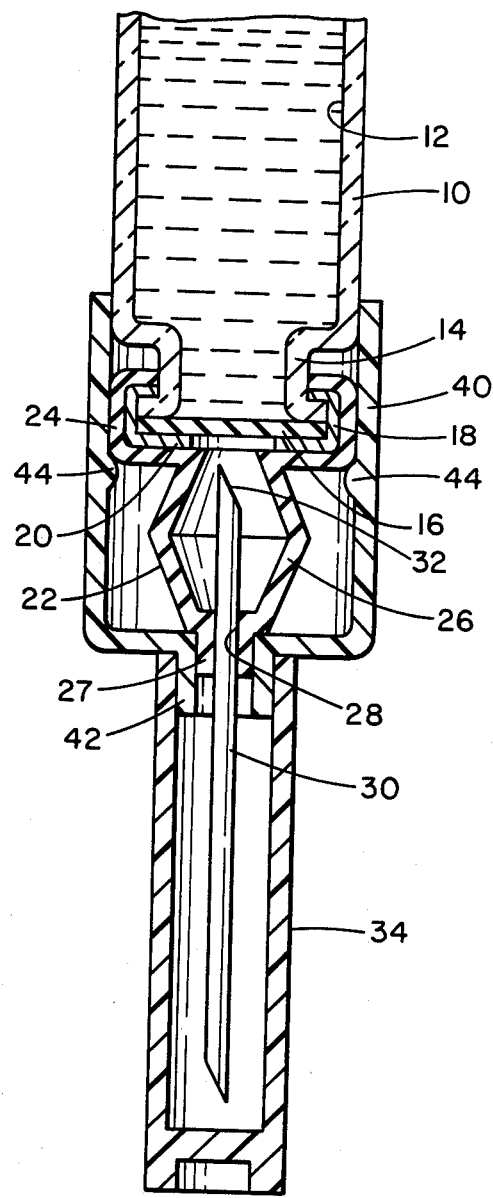

United States Patent [19]

Cohen

[11] 4,303,069

[45] Dec. 1, 1981

[54] HYPODERMIC SYRINGE WITH NEEDLE GUIDE

[76] Inventor: Milton J. Cohen, 10823 Burbank Dr., Potomac, Md. 20854

[21] Appl. No.: 133,569

[22] Filed: Mar. 24, 1980

Related U.S. Application Data

[63] Continuation-in-part of Ser. No. 956,102, Oct. 30, 1978, abandoned.

[51] Int. Cl.³ .............................................. A61M 5/00
[52] U.S. Cl. .................................................. 128/218 N
[58] Field of Search ....... 128/218 N, 218 D, 218 DA, 128/220, 221, 215, 216; 206/365

[56] References Cited

U.S. PATENT DOCUMENTS

| | | | |
|---|---|---|---|
| 2,642,064 | 6/1953 | Lawshe | 128/216 |
| 2,728,341 | 12/1955 | Roehr | 128/218 D |
| 2,828,743 | 4/1958 | Ashkenaz et al. | 128/218 D |
| 3,026,873 | 3/1967 | Miskel et al. | 128/218 D |
| 3,557,787 | 1/1971 | Cohen | 128/220 |
| 3,736,932 | 6/1973 | Satchell | 128/218 R |
| 4,221,218 | 9/1980 | Pfleger | 128/218 D |

Primary Examiner—John D. Yasko
Attorney, Agent, or Firm—McDougall, Hersh & Scott

[57] ABSTRACT

A syringe having a sealed member at one end and in which a hypodermic needle is mounted by a collapsible hub with the rearward end of the needle terminating a short distance in advance of the sealing member means for guiding the collapsible hub and needle for axial movement in the direction for displacement of the needle in the direction for piercing the sealing member, means for retaining the collapsible hub in needle piercing position and means for removing a cover from the needle to expose the needle while in needle piercing position.

5 Claims, 2 Drawing Figures

U.S. Patent     Dec. 1, 1981     4,303,069

HYPODERMIC SYRINGE WITH NEEDLE GUIDE

This invention is a continuation-in-part of my copending application Ser. No. 956,102, filed Oct. 30, 1978, and entitled "Hypodermic Syringe with Needle Guide" now abandoned.

This invention relates to a device for injection of a liquid in the form of a solution or dispersion. The invention has to do particularly with materials, such as medicaments, which cannot be premixed without deterioration, loss of activity or the like and, therefore, are required to be mixed in measured amounts immediately prior to use, as by injection.

In my previously issued U.S. Pat. No. 3,838,689, description is made of a syringe suitable for use in the injection of materials of the type described, which are maintained in measured amounts in a separated relation, and admixed one with the other immediately prior to use. In the aforementioned patent, use is made of a syringe formed of one vial telescoped within another in which the solid or liquid component to be admixed with a liquid phase is contained in the one vial, while the liquid phase to be combined with the solid or liquid is contained in the other vial which receives the one vial in telescoping relation. The one vial is sealed at one end by a rupturable membrane and a hollow needle for support in position to rupture the sealing membrane when the materials are mixed and ready for injection.

The telescoping end portion of the other vial is provided with a sealing ring that extends into sealing engagement with the inner walls of the one vial to enable the telescoping vial to move axially within the telescoped one vial as a piston.

The telescoping end of the other vial is provided with a sealing member having a slit which is adapted to be opened in response to pressure from the liquid contained in the other vial and the other vial is provided with a piston in sealing engagement with the inner walls but in spaced relation with the sealed end portion to confine the liquid therebetween. The piston member is provided with means for actuation to displace the piston plug axially in the other vial.

In operation, responsive to displacement of the piston plug in the direction towards the telescoping end portion of the other vial, pressure is imposed on the confined liquid phase whereby the liquid phase is forced from the other vial through the slit into the first vial for admixture with material contained therein. Upon transfer of the measured amount of liquid phase from the other vial, the unit is shaken to effect mixture of the material for uniform dispersion or solution. Thereafter, the hypodermic needle is released to pierce the sealing membrane on the end of the first vial to enable the mixed materials to be displaced from the vial and through the hypodermic needle in response to pressure applied as the telescoping vial is actuated as a piston for actuating movement through the first vial.

In my U.S. Pat. No. 4,055,177, a description is made of a syringe of the type described but wherein use is made of a single tubular member which is subdivided by a rupturable disc member, in the form of a slideable piston plug, into a rearward compartment for housing the liquid phase and a forward compartment for housing the liquid, solid or the like material to be dissolved, dispersed, or otherwise admixed with the liquid phase, with the compartments separated in sealing relation by the rupturable disc member.

A piston plug is mounted in the tubular member adjacent the rupturable disc member with a hollow needle extending from the piston plug in the direction towards the rupturable sealing member whereby the needle penetrates the sealing member responsive to relative axial movement to bring the needle into engagement to penetrate the rupturable disc member whereby communication is established between the chambers to enable the liquid phase to flow from the rearward chamber into the forward chamber responsive to axial displacement of a piston plug in the direction towards the forward end of the tubular member.

In both devices of the type described, the forward end of the tubular member is sealed by a rupturable membrane adapted to be pierced by a hollow needle after the material in the two compartments have been combined in the forward compartment. In the device described in the aforementioned U.S. Pat. No. 4,055,177, the hollow needle is mounted with the rearward end portion immediately in advance of the rupturable membrane in position to pierce the membrane in response to spring tension when released upon removal of the needle cover. Such mounting of the hollow needle in a pretensioned release for release upon removal of the cover represents an assembly which makes use of a large number of parts that are difficult to assemble and which pose a danger because the needle can function as a dart when accidently released under tension during the assembly.

This particular problem is overcome in the device described in my previously issued U.S. Pat. No. 3,413,974 wherein the hollow needle is mounted without tension in position of use to penetrate the sealing membrane. In the device described, use is made of a collapsible hub mounted on the forward end of the tubular member whereby the needle is supported by the hub with the rearward end terminating a short distance in advance of the rupturable membrane. In use, the hub is collapsed manually to effect relative axial movement of the needle in a direction to project the rearward end of the needle through the sealing membrane and into the compartment for direct communication with the interior.

Conversion to an untensioned needle and reliance on manual operation to collapse the hub and push the hollow needle through the membrane sealing the end of the vial has not found widespread acceptance for a number of reasons. One noticeable defect stems from the flexibility of the hub by which the needle is supported with the result that the needle can be displaced to pierce the sealing membrane at various angles relative to the aligned axis of the tubular member. As a result, difficulties are sometimes experienced in positioning the needle through the sealing membrane or penetration may be effected at a location which detracts from the desired removal of liquid content material from the tubular member.

Such misalignment also positions the hollow needle at an angle that may interfere with the subsequent use of the device for the infusion of the content material into the desired location or vessel of the body.

Thus it is an object of this invention to produce a syringe of the type described wherein means are provided for guiding the needle for axial displacement for proper penetration of the sealing membrane and for maintaining the needle in a proper axial alignment for use as the syringe.

Figure 2:
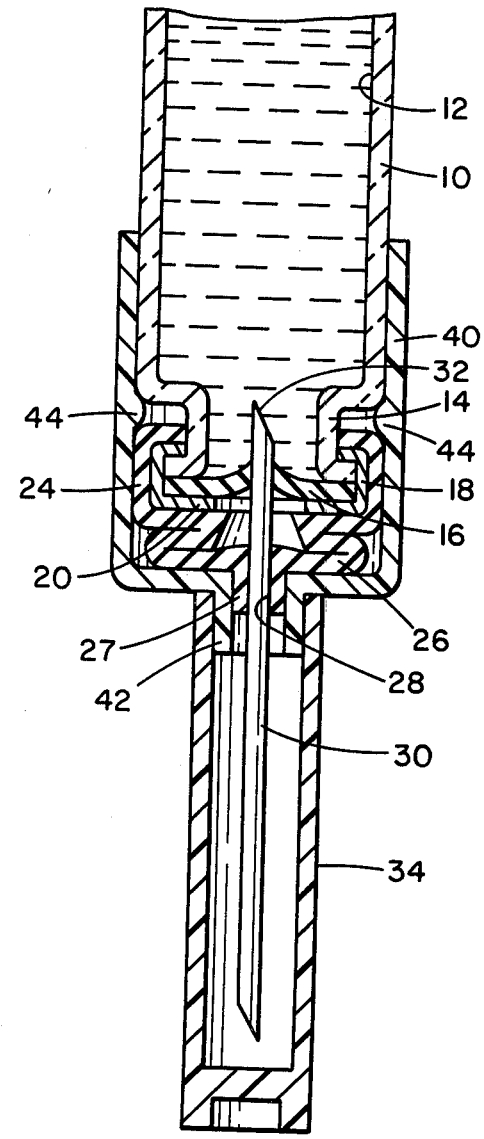

These and other objects and advantages of this invention will hereinafter appear and for purposes of illustration, but not of limitation, an embodiment of the invention is shown in the accompanying drawing in which:

FIG. 1 is a sectional elevational view of a portion of the device embodying the features of this invention, and FIG. 2 is a sectional elevational view similar to that of FIG. 1 showing the elements in their respective positions responsive to displacement of the needle to pierce the sealing membrane.

Since the assembly embodying the features of this invention is not limited to use with syringes of the types described in the aforementioned patents, but in addition, finds use in syringes formed of a single barrel for use in injections of liquid medicaments or materials or for the withdrawal of blood or other body fluids, it will be sufficient to describe the invention with respect to the needle and its support by a collapsible hub mounted on the sealed end portion of the vial.

With reference now to the drawing, the description will be limited to the assembly of the hollow needle and its supporting hub mounted on the sealed end portion of a tubular member which may constitute the outer vial in a wet-dry syringe of the type described in U.S. Pat. No. 3,838,689, or the sealed end of the single vial of the type described in U.S. Pat. No. 4,055,177, or the sealed end of a single tubular member employed in a conventional syringe for the injection or withdrawal of fluids.

In the illustrated modification, the tubular member 10 can be formed of glass, plastic or the like having a bore 12 extending therethrough to a neck portion 14 of smaller cross section at the forward end. The forward end is sealed by means of a disc member 16 held in place in sealing relation across the open neck 14 of the tubular member 10 by means of a metal cap 18 which is crimped about the outer neck portion of the tubular member while the inner portion 20 of the cap overlaps the outer edge portion of the sealing disc member overlying the flattened end surface of the tubular member 10. A hub member 22 has a skirt portion 24 crimped about the skirt portion of the cap 18 for securing the hub onto the neck end portion of the tubular member. The hub 22 is also provided with an intermediate collapsible or corrugated portion 26 extending forwardly in axial alignment with the forward end of the tubular member 10 with the forward end portion of the hub terminating in a tubular member 27 of reduced cross section having a passage 28 through which a hollow needle 30 extends with a sharpened end portion 32 of the needle projecting into the interior of the hub member 22 for a distance less than the spaced relation between the hub end 28 and the sealing disc member 16, when in normal position, thereby to locate the rearward end of the needle immediately in advance of the center of the disc member.

The needle and hub are protected, other than when in position of use, by a cover 34 in the form of a tubular member closed at its outer end and open at the inner end to enable the portion of the needle beyond the hub to extend into the bore.

In use, it is only necessary first to displace the cover rearwardly to collapse the hub and project the needle through the sealing disc 16 and then displace the cover forwardly to remove the cover and expose the forwardly projecting portion of the needle in position of use. To the present, the device described corresponds to the construction illustrated in my previously issued U.S. Pat. No. 3,838,689.

For this purpose, use is made of a sleeve member 40 having a bore dimensioned and shaped to correspond to the outside dimension and shape of the tubular member 10 to enable the sleeve to receive the end portion of the tubular member in telescoping relation therein for relative axial sliding movement. The forward end portion of the sleeve section 40 is provided with a short sleeve section 42 of greatly reduced cross section for receipt of the tubular member 27 of reduced cross section of the hub 22. The open end of the needle cover 34 makes a sliding fit with the short sleeve section 42 which is received in telescoping relation in the open end thereof.

In accordance with the practice of this invention, means are provided for guiding the collapsible hub in axial movement during displacement of the needle to pierce the sealing disc 16 including means for properly locating the hub and guide means properly to position the needle in assembly, means for latching the needle hub in collapsed position to retain the needle to extend through the pierced sealing disc, and for removal of the needle cover while the collapsible hub is retained in collapsed position to enable material to be dispensed from the tubular member through the needle.

The sleeve section 40 is dimensioned to have a length to engage the forward end portion of the tubular member 10 in telescoping relation with a portion extending forwardly thereof, at least as great as the amount of collapse of the hub member required to project the needle point 32 through the sealing disc 16 and into the bore of the tubular member 10.

The interior surface of the sleeve section 40 is provided with at least one and preferably two or more oppositely disposed projections 44 positioned to abut the sealed end portion of the tubular member when the needle is in proper location for piercing the sealing disc.

In use, the assembly is packaged with the needle cover 34 telescoped over the end of the tubular section 42 of the sleeve guide with the tubular section 27 of the collapsible hub seated within the sleeve section 42 for conjoint movement therewith. To establish communication with the interior of the vial, the needle cover is manually displaced in the inward direction. By reason of the sliding engagement of the sleeve 40 in telescoping relation with the outer wall of the tubular member 10, the needle and cover are guided in axial alignment during displacement to pierce the sealing disc 16.

During such movement, the abutment(s) 44 slides along the sealing members until it clears the neck portion and snaps into the recessed portion whereby the collapsible hub is latched in collapsed position to retain the needle in pierced position. With the needle hub latched in collapsed position, the needle cover 34 can be withdrawn to free the needle while the inner end is still located within the bore of the tubular member.

The distance between the neck portion and the sealed end of the tubular member should be greater than the distance between the end 32 of the needle and the sealing disc 16 so that the amount of displacement of the abutments before entry into the recessed neck portions will be greater than the amount of travel of the needle to pierce the sealing disc.

Sufficient flexibility to accommodate the flexure caused by displacement of the abutments over the sealed end portion can be provided by forming the sleeve of a deformable plastic and/or by providing sliding grooves in the sealed end portion of the tubular member and/or by making use of resilient fingers in tubular arrangement.

Instead of a sliding fit, the needle cover can be otherwise removably secured to the sleeve guide, as by threaded engagement, clip engagement or the like.

It will be understood that the sleeve can be joined to form an integral part of the needle cover or otherwise connected thereto for conjoint movement therewith. It will also be understood that the desired guidance in axial movement can be achieved when, instead of a sleeve, use is made of a bracket formed of at least three rods circumferentially arranged to make sliding contact with the outer wall of the tubular member whereby the bracket is guided for axial movement relative to the tubular member.

It will be understood that changes may be made in the details of construction, arrangement and operation, without departing from the spirit of the invention, especially as defined in the following claims.

I claim:

1. A syringe assembly comprising a tubular member, a rupturable closure sealing the forward end of the tubular member an elongate hollow hypodermic needle, and collapsible hub member formed of flexible material connected at one end to the forward end of the tubular member, the other end being of reduced cross section with a passage therethrough through which an intermediate portion of the needle extends for conjoint movement therewith, with the rearward end of the needle terminating a short distance in advance of the rupturable closure when the hub member is in uncollapsed position and penetrating through the rupturable closure when in collapsed position, the improvement which comprises a tubular guide member having an open end in telescoping engagement with the forward end portion of the tubular member to enable relative sliding movement in the axial direction, the other end having an inwardly extending bottom wall portion terminating in a sleeve section into which the reduced cross section of the hub member extends for engagement therewith, an elongate cover dimensioned to have a length greater than the length of the needle extending outwardly of the hub, said cover being closed at one end and open at the other end with the opening being dimensioned slidably to be received on the sleeve section of the bottom wall of the tubular guide, and an operative engagement between the other end of said tubular guide member and the other end of the collapsible member for conjoint movement therewith for axial guidance of the hub and needle during displacement to collapsed position, means for latching the hub in collapsed position to retain the hub member in collapsed position with the needle extending through the rupturable closure while the needle cover is removed from the sleeve section to expose the needle.

2. A syringe as claimed in claim 1 which includes a removable cover for the needle.

3. A syringe as claimed in claim 1 in which the guide member is in the form of a cylindrical section in which the forward end portion of the tubular member is received in telescoping relation.

4. A syringe as claimed in claim 3 which includes recessed portions in the tubular member spaced axially from the forward end thereof and in which the means for latching the collapsible hub in collapsed position comprises one or more abutments projecting from the inner surface of the tubular guide member for receipt of said projections in the recessed portion of the tubular member when the collapsible hub is displaced to collapsed position.

5. A syringe as claimed in claim 4 in which the tubular member is formed with a neck portion of reduced cross section, and the recessed portions are spaced from the neck portion by an amount corresponding to the axial displacement of the hub for penetrating the needle through the sealing disc in collapsed position.

* * * * *